(12) United States Patent  
Tezuka et al.

(10) Patent No.: US 10,478,079 B2  
(45) Date of Patent: Nov. 19, 2019

(54) PULSE ESTIMATION DEVICE, PULSE ESTIMATION SYSTEM, AND PULSE ESTIMATION METHOD

(71) Applicant: PANASONIC INTELLECTUAL PROPERTY MANAGEMENT CO., LTD., Osaka (JP)

(72) Inventors: Tadanori Tezuka, Fukuoka (JP); Tsuyoshi Nakamura, Fukuoka (JP); Masatoshi Matsuo, Fukuoka (JP)

(73) Assignee: PANASONIC INTELLECTUAL PROPERTY MANAGEMENT CO., LTD., Osaka (JP)

( * ) Notice: Subject to any disclaimer, the term of this patent is extended or adjusted under 35 U.S.C. 154(b) by 97 days.

(21) Appl. No.: 15/580,925

(22) PCT Filed: May 10, 2016

(86) PCT No.: PCT/JP2016/002277  
§ 371 (c)(1),  
(2) Date: Dec. 8, 2017

(87) PCT Pub. No.: WO2016/203697  
PCT Pub. Date: Dec. 22, 2016

(65) Prior Publication Data  
US 2018/0310844 A1    Nov. 1, 2018

(30) Foreign Application Priority Data

Jun. 15, 2015 (JP) .................................. 2015-120333

(51) Int. Cl.  
*A61B 5/024* (2006.01)  
*G06T 7/11* (2017.01)  
(Continued)

(52) U.S. Cl.  
CPC ............ *A61B 5/02427* (2013.01); *G06T 7/11* (2017.01); *G06T 7/174* (2017.01);  
(Continued)

(58) Field of Classification Search  
CPC ......... G06T 7/11; G06T 7/14; A61B 5/02427; A61B 5/0077; A61B 5/02416; A61B 5/7485  
See application file for complete search history.

(56) References Cited

U.S. PATENT DOCUMENTS

| | | | |
|---|---|---|---|
| 2010/0172567 A1* | 7/2010 | Prokoski | A61B 5/0064 382/132 |
| 2011/0149120 A1* | 6/2011 | Kubota | H04N 5/232 348/240.99 |

(Continued)

FOREIGN PATENT DOCUMENTS

| | | |
|---|---|---|
| JP | 2002-228939 | 8/2002 |
| JP | 2002-300603 | 10/2002 |

(Continued)

OTHER PUBLICATIONS

Bousefsaf ("Continuous wavelet filtering on webcam photoplethysmographic signals to remotely assess the instantaneous hear rate") Biomedical Signal Processing and Control (2013). (Year: 2013).*

(Continued)

*Primary Examiner* — Kim Y Vu  
*Assistant Examiner* — Molly Delaney  
(74) *Attorney, Agent, or Firm* — Greenblum & Bernstein, P.L.C.

(57) ABSTRACT

A pulse can be stably estimated based on an image data suitable for extracting a pulse signal. A pulse estimation device includes image input portion (21) to which time-sequential captured images including at least a portion of (Continued)

subject H as an object are input from camera (2); region extractor (22) that extracts a skin-color region from each of the captured images; zoom commander (28) that transmits a zoom command to camera (2) that has imaged the captured images or a user of camera (2) in order to adjust a size of the skin-color region; and pulse estimator (23) that estimates a pulse of subject H based on the skin-color region of the captured images obtained by imaging with camera (2), after the zoom command is transmitted.

13 Claims, 11 Drawing Sheets

(51) Int. Cl.
*G06T 7/174* (2017.01)
*H04N 5/232* (2006.01)

(52) U.S. Cl.
CPC ... *H04N 5/23296* (2013.01); *H04N 5/232127* (2018.08); *H04N 5/232939* (2018.08); *A61B 2562/0233* (2013.01); *A61B 2576/00* (2013.01); *G06T 2207/10016* (2013.01); *G06T 2207/10024* (2013.01); *G06T 2207/30004* (2013.01)

(56) References Cited

U.S. PATENT DOCUMENTS

| | | | | |
|---|---|---|---|---|
| 2015/0011851 A1* | 1/2015 | Mehta | ............... | A61B 5/7221 600/324 |
| 2015/0366456 A1* | 12/2015 | Takamori | ............ | A61B 5/6898 600/480 |
| 2016/0015308 A1* | 1/2016 | Kirenko | ............... | A61B 5/721 600/301 |
| 2016/0302735 A1* | 10/2016 | Noguchi | ............ | A61B 5/6898 |
| 2017/0112382 A1* | 4/2017 | Nakata | .............. | A61B 5/00 |
| 2018/0256047 A1* | 9/2018 | Mori | ................. | G06T 7/0012 |

FOREIGN PATENT DOCUMENTS

| | | |
|---|---|---|
| JP | 2005-218507 | 8/2005 |
| JP | 2010-057718 | 3/2010 |
| JP | 2012-239661 | 12/2012 |
| WO | 2013/128345 A1 | 9/2013 |

OTHER PUBLICATIONS

International Search Report issued in International Patent Application No. PCT/JP2016/002277, dated Jul. 26, 2016, along with an english translation thereof.

The Extended European Search Report dated May 15, 2018 for the related European Patent Application No. 16811178.9.

* cited by examiner

CAPTURED IMAGE (BEFORE ZOOM)

CAPTURED IMAGE (AFTER ZOOM)

FIG. 7A
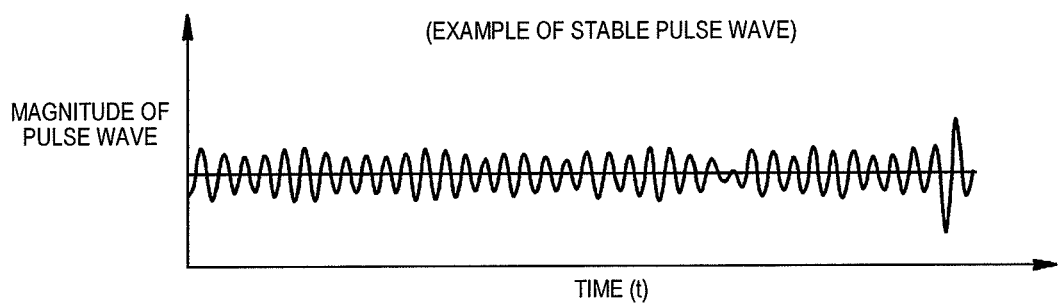
(EXAMPLE OF STABLE PULSE WAVE)
FIG. 7B
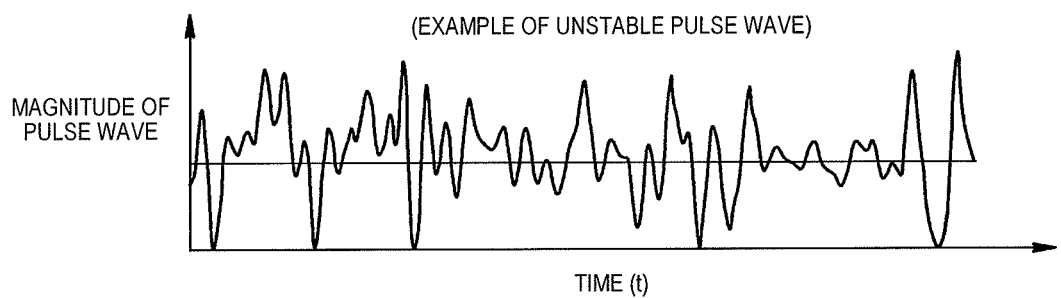
(EXAMPLE OF UNSTABLE PULSE WAVE)
FIG. 8A
(EXAMPLE OF STABLE PULSE WAVE)
| 70 | 72 | 68 | 71 | 73 | 71 | 70 | • • • |
FIG. 8B
(EXAMPLE OF UNSTABLE PULSE WAVE)
| 70 | 30 | 90 | 60 | - | 90 | 20 | • • • |

PULSE ESTIMATION DEVICE, PULSE ESTIMATION SYSTEM, AND PULSE ESTIMATION METHOD

TECHNICAL FIELD

The present disclosure relates to a pulse estimation device, a pulse estimation system, and a pulse estimation method which estimate a pulse of a human body from information obtained without contact with the human body.

BACKGROUND ART

In the related art, for measuring a pulse of a human, a method in which a measurer (such as a nurse) manually checks a pulsation by contacting a wrist of a subject with a finger, a method in which a dedicated measuring equipment is attached to a wrist, a finger, or the like of a subject so as to automatically detect the pulsation, and the like are known. On the other hand, in these measuring method, free behavior of a subject is temporarily restricted or there is need to attach measuring equipment on a subject. Therefore, a technology for estimating (detecting) a pulse without contact with a subject (human body) is developed.

For example, in a technology of detecting a heart rate (in general, equivalent to a pulse rate) without contact with a human body, a heart rate detection device, that automatically detects the heart rate, is known in which spectrum density of a time series signal is extracted from an image data obtained by imaging a subject, and a peak frequency caused by a heartbeat signal is specified from the spectrum density (refer to PTL 1).

In addition, in a technology of calculating the heart rate from an acquired pulse wave, for example, a photometric device for a living body is known in which a light detector detects a light that has emitted from a light irradiator and transmitted through an inside of a subject, and the heart rate is calculated from two continuous peaks of the pulse wave shown in a measurement signal obtained by the light detector (refer to PTL 2).

CITATION LIST

Patent Literature

PTL 1: Japanese Patent Unexamined Publication No. 2012-239661
PTL 2: Japanese Patent Unexamined Publication No. 2010-57718

SUMMARY OF THE INVENTION

As shown in the related art disclosed in PTL 1, in a case where the pulse is estimated from a facial image or the like imaged by a camera, a fluctuation amount (that is, a fluctuation amount of a pixel value) of a pulse signal extracted from an image data is minute. Therefore, there are problems in that, depending on performance of the camera or imaging condition (brightness or the like), a good pulse signal cannot be extracted (that is, an image data suitable for extracting the pulse signal cannot be acquired), and it becomes difficult to estimate a pulse stably. These problems can similarly occur also in a case of using the related art as disclosed in PTL 2 as a method of detecting the pulse from the pulse signal.

The present disclosure is proposed in consideration of these problems of the related art, a main object of the present disclosure is to provide a pulse estimation device, a pulse estimation system, and a pulse estimation method which can stably estimate a pulse based on an image data suitable for extracting a pulse signal.

A pulse estimation device of the present disclosure that estimates a pulse of a subject from information obtained without contact with the subject, the device includes an image input portion to which time-sequential captured images including at least a portion of the subject as an object are input from a camera; a region extractor that extracts a skin-color region from each of the captured images; a zoom commander that transmits a zoom command to the camera that has imaged the captured images or a user of the camera in order to adjust a size of the skin-color region; and a pulse estimator that estimates the pulse of the subject based on the skin-color region of the captured images obtained by imaging with the camera, after the zoom command is transmitted.

According to the present disclosure, it is possible to estimate a pulse stably based on an image data suitable for extracting a pulse signal.

BRIEF DESCRIPTION OF DRAWINGS

FIG. 7A is an explanatory diagram of a pulse determining process executed by a pulse calculator of a pulse estimation device shown in FIG. 6.
FIG. 7B is an explanatory diagram of the pulse determining process executed by the pulse calculator of the pulse estimation device shown in FIG. 6.
FIG. 8A is an explanatory diagram illustrating a modification example of the pulse determining process shown in FIG. 7A.
FIG. 8B is an explanatory diagram illustrating a modification example of the pulse determining process shown in FIG. 7B.

DESCRIPTION OF EMBODIMENTS

Figure 1:
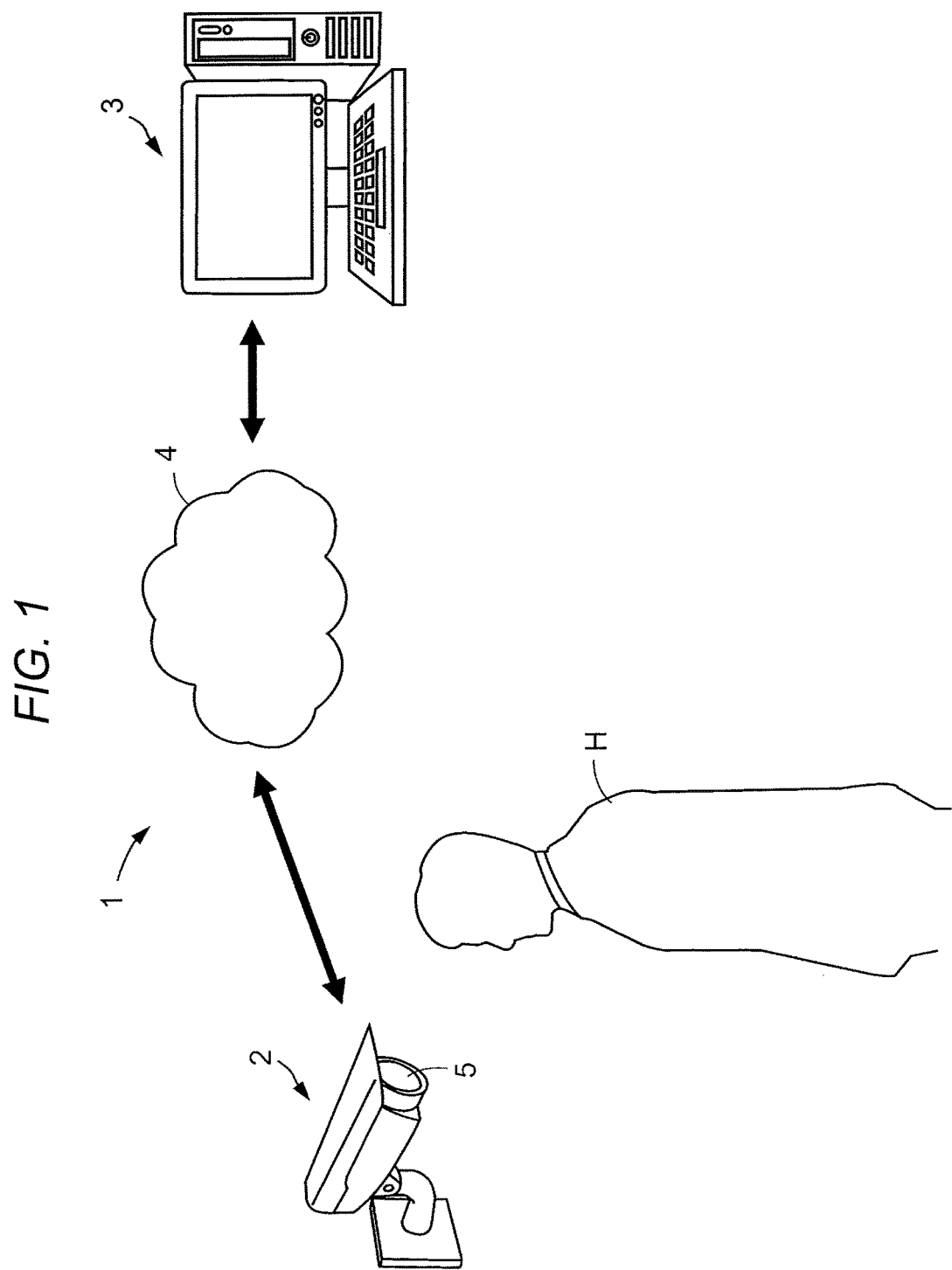
FIG. 1 is an overall configuration diagram of a pulse estimation system of a first embodiment.

In a first disclosure for solving the above problem, a pulse estimation device that estimates a pulse of a subject from information obtained without contact with the subject, the device includes an image input portion to which time-sequential captured images including at least a portion of the subject as an object are input from a camera; a region extractor that extracts a skin-color region from each of the captured images; a zoom commander that transmits a zoom command to the camera that has imaged the captured images or a user of the camera in order to adjust a size of the skin-color region; and a pulse estimator that estimates the pulse of the subject based on the skin-color region of the captured images obtained by imaging with the camera, after the zoom command is transmitted.

According to the pulse estimation device of the first disclosure, since a zoom command is transmitted to the camera or a user of the camera and then the pulse is estimated based on the captured image that is obtained by imaging with the camera, it is possible to estimate the pulse stably based on the image data suitable for extracting the pulse signal.

In a second disclosure, the pulse estimation device of the first disclosure, further includes a region determiner that determines whether or not the size of the skin-color region satisfies a preset reference range. In a case where the region determiner determines that the size of the skin-color region does not satisfy the reference range, the zoom commander transmits the zoom command to the camera or a user of the camera.

According to the pulse estimation device of the second disclosure, since the zoom command is appropriately transmitted to the camera that has imaged the captured images or the user of the camera based on the determination result of the region determiner that determines whether or not the size of the skin-color region satisfies the reference range, it is possible to estimate the pulse stably.

In a third disclosure, the region determiner of the second disclosure sets the size of the skin-color region based on the number of pixels constituting the skin-color region of the captured image, and determines whether or not the number of pixels satisfies a preset reference range of the number of pixels.

According to the pulse estimation device of the third disclosure, since the size of the skin-color region is set based on the number of pixels constituting the skin-color region, the skin-color region is easily extracted. As a result, it is possible to estimate the pulse stably by simple process.

In a fourth disclosure, the region determiner of the second or third disclosure changes the reference range according to performance of an image sensor of the camera.

According to the pulse estimation device of the fourth disclosure, since reference range for adjusting the size of the skin-color region is changed based on the performance of the image sensor, it is possible to acquire the image data more suitable for extracting the pulse signal. As a result, it is possible to estimate the pulse more stably.

In a fifth disclosure, the region determiner of the second or third disclosure changes the reference range according to an exposure condition of the captured image.

According to the pulse estimation device of the fifth disclosure, since reference range for adjusting the size of the skin-color region is changed based on the exposure condition during imaging, it is possible to acquire the image data more suitable for extracting the pulse signal. As a result, it is possible to estimate the pulse more stably.

In a sixth disclosure, the pulse estimator of the first disclosure estimates the pulse of the subject based on the captured images before the zoom command is transmitted, and determines whether or not the estimated pulse is stable, and in a case where the pulse estimator determines that the pulse is not stable, the zoom commander transmits the zoom command.

According to the pulse estimation device of the sixth disclosure, since the zoom command can be appropriately transmitted to the camera that has imaged the captured images or a user of the camera based on the determination result (that is, whether or not the estimated pulse is stable) of the pulse estimator, it is possible to estimate the pulse more stably.

In a seventh disclosure, the region extractor of any one of the first to sixth disclosures extracts a face region of the subject on the captured image as the skin-color region.

According to the pulse estimation device of the seventh disclosure, since the face region of the subject is extracted as the skin-color region, it becomes to easily extract the skin-color region. As a result, it is possible to estimate the pulse stably by simple process.

In an eighth disclosure, the pulse estimation device of any one of the first to seventh disclosures, further includes a display that displays a demand for adjusting the size of the skin-color region to the user based on the zoom command to the user.

According to the pulse estimation device of the eighth disclosure, it is possible to reliably perform the zoom operation of the camera by the user.

In a ninth disclosure, a pulse estimation system includes the pulse estimation device of any one of first to eight disclosures; and the camera that performs a predetermined zoom operation based on the zoom command.

According to the pulse estimation system of the ninth disclosure, it is possible to estimate the pulse stably based on the captured image input to the image input portion after the zoom command is transmitted to the camera or the user.

In a tenth disclosure, a pulse estimation method of estimating a pulse of a subject from information obtained without contact with the subject, the method includes a step of inputting time-sequential captured images including at least a portion of the subject as an object are input from a camera; a step of extracting a skin-color region from each of the captured images; a step of transmitting a zoom command to the camera that has imaged the captured images or a user of the camera in order to change a size of the skin-color region such that the size of the skin-color region satisfies a preset reference range; and a step of estimating a pulse of the subject based on the skin-color region of each the captured images obtained by the camera, after the zoom command is transmitted.

According to the pulse estimation method of the tenth disclosure, it is possible to estimate the pulse stably based on the captured images input to the image input portion after the zoom command is transmitted to the camera.

Hereinafter, embodiments of the present disclosure will be described with reference to the drawings.

First Embodiment

Figure 2:
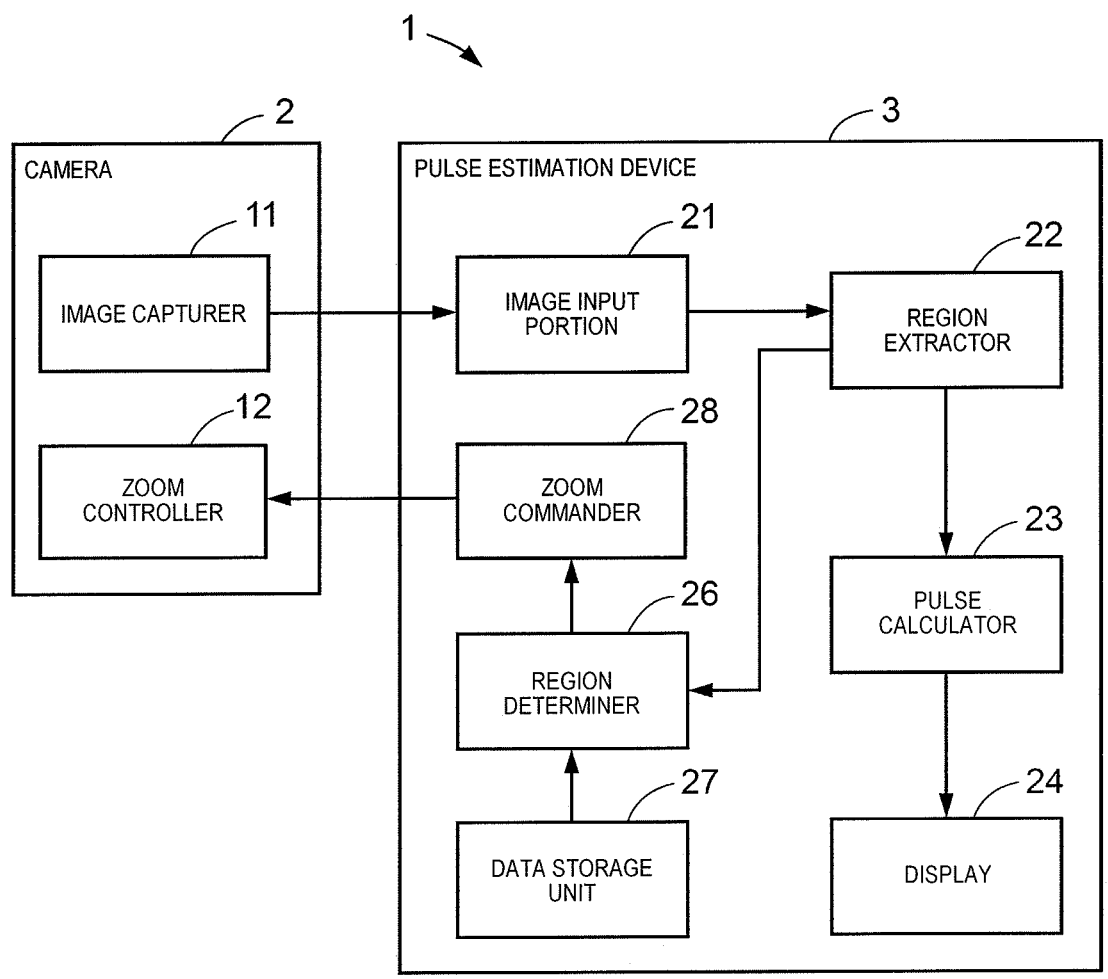
FIG. 2 is a functional block diagram of the pulse estimation system of the first embodiment.
Figure 3:
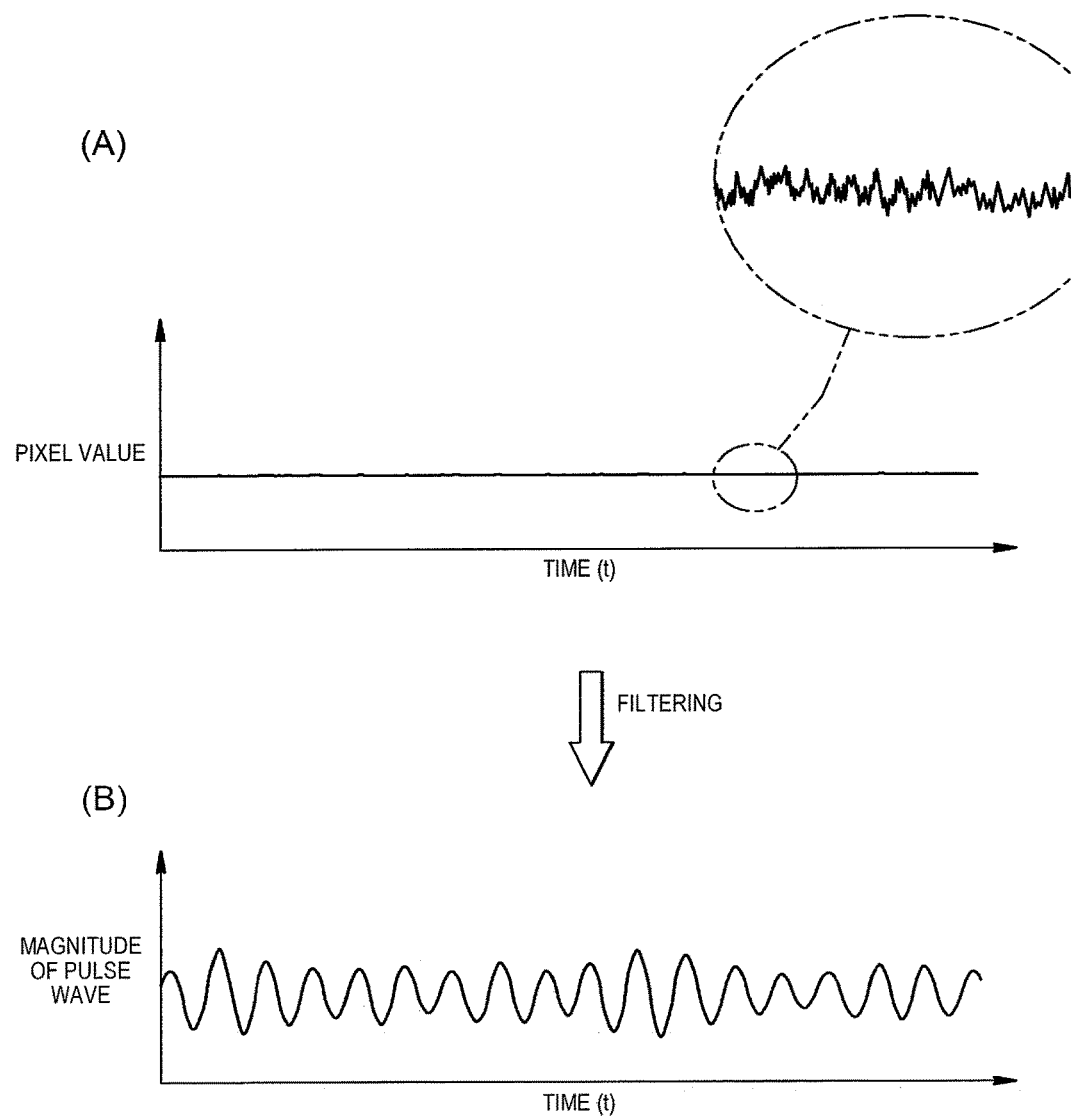
FIG. 3 is an explanatory diagram of a pulse extracting process by a pulse calculator of a pulse estimation device shown in FIG. 2.
Figure 4A:
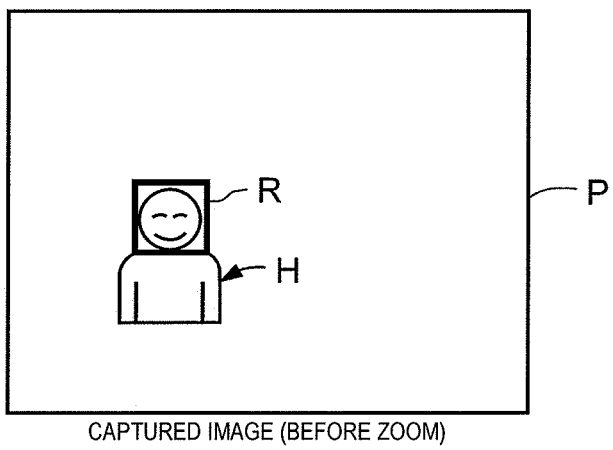
FIG. 4A is an explanatory diagram of a result of control by a zoom commander of the pulse estimation device shown in FIG. 2.
Figure 4B:
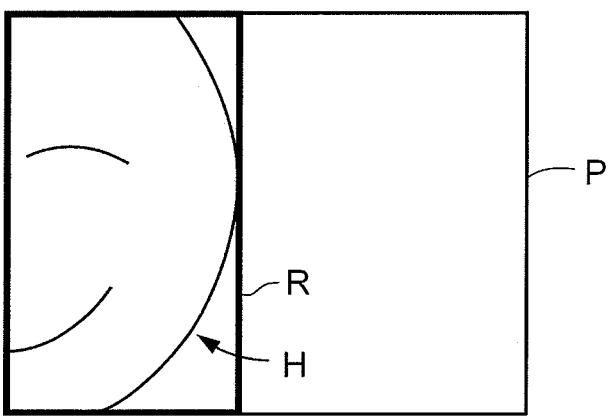
FIG. 4B is an explanatory diagram of a result of control by the zoom commander of the pulse estimation device shown in FIG. 2.
Figure 4C:
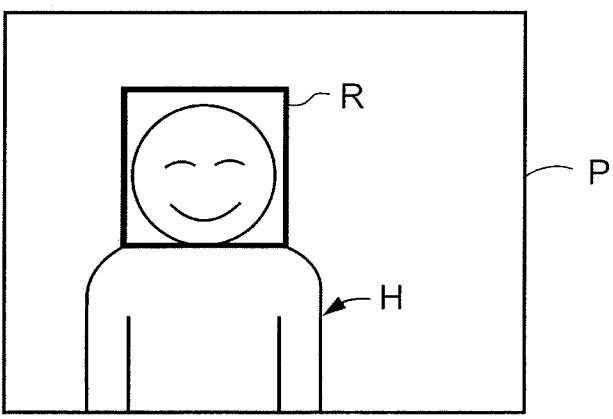
FIG. 4C is an explanatory diagram of a result of control by the zoom commander of the pulse estimation device shown in FIG. 2.

FIGS. 1 and 2 are respectively an overall configuration diagram and a functional block diagram of pulse estimation system 1 according to the first embodiment of the present disclosure. FIG. 3 is an explanatory diagram of a pulse extracting process by pulse calculator 23 of pulse estimation device 3. FIGS. 4A to 4C are explanatory diagrams of result of control by zoom commander 28 of pulse estimation device 3 shown in FIG. 2.

Pulse estimation system 1 estimates a pulse of a human body from information (captured image) obtained without contact with the human body. As shown in FIG. 1, the pulse estimation system 1 includes camera 2 imaging at least a portion of human (subject) H as an object and pulse estimation device 3 estimating a pulse (pulse rate or pulse wave) of human H from a captured image obtained by imaging with camera 2. In addition, in pulse estimation system 1, camera 2 and pulse estimation device 3 are connected to each other via network 4 such as the Internet or a local area network (LAN) in a communication-enabled manner. However, the configuration is not limited thereto, camera 2 and pulse estimation device 3 may be connected directly to each other through the known communication cable in a communication-enabled manner.

Camera 2 is a video camera including known zoom lens mechanism 5. As shown in FIG. 2, camera 2 includes image capturer 11 that causes light from an object which is obtained through zoom lens mechanism 5 to form an image on an image sensor (such as CCD and CMOS) (not illustrated) so as to output a video signal, which is obtained by converting the light of the formed image to an electronic signal, to pulse estimation device 3, and zoom controller 12 that controls optical zoom operation of zoom lens mechanism 5. Image capturer 11 is capable of performing the known signal processing for noise suppression, edge emphasis, and the like. Although only one camera 2 is illustrated in FIG. 1, pulse estimation system 1 can also have a configuration in which a plurality of similar cameras are provided.

Pulse estimation device 3 includes image input portion 21 to which a video signal from image capturer 11 is input as the time-sequential captured images (data of frame image) including at least a portion of human H, region extractor 22 that extracts the skin-color region (here, the face region) of human H from each of the captured image, and pulse calculator (the pulse estimator) 23 that calculates the pulse of human H based on the extracted skin-color region of human H, and display 24 that includes the known display device capable of displaying the various information including the pulse estimation result to the user of pulse estimation device 3. The skin-color region extracted by region extractor 22 is a skin-exposed region of the human body, and it is possible to estimate the pulse from the data of the captured image of the region.

Pulse estimation device 3 includes region determiner 26 that determines whether or not the size of the skin-color region extracted by region extractor 22 satisfies the preset reference range, data storage unit 27 that stores various data including the reference range, necessary for the pulse estimation, and zoom commander 28 that transmits the zoom command to zoom controller 12 of camera 2 in order to adjust the size of the skin-color region based on the determination result of region determiner 26.

Region extractor 22 executes a known face-detecting process, by which a feature amount of the face is recognized, with respect to the each captured image (frame image). Thus, region extractor 22 extracts and tracks the detected face region as the skin-color region of human H. Region extractor 22 transmits the data of captured image relating to the extracted face region to pulse calculator 23 and transmits the data relating to the size of the face region (here, the number of pixels constituting the skin-color region) to region determiner 26.

A method used by region extractor 22 is not limited to the method above described. Region extractor 22 may extract a pixel including a preset skin-color component (for example, a preset rate of each pixel value of RGB, the rate being a value that varies depending on races) from the captured image, and a region from which the pixel is extracted may be set as the skin-color region. In this case, even a portion (for example, hand or arm) in which skin other than the face is exposed can be extracted as the skin-color region. However, as described above, it is advantageous in that the skin-color region can be easily extracted by extracting the face region of human H as the skin-color region. Only one human H is illustrated in FIG. 1; however, in a case where a plurality of humans are included in the captured image, region extractor 22 can extract a plurality of face regions.

Pulse calculator 23 calculates, for example, a pixel value (0 to 255 gradations) of each component of RGB with respect to respective pixels constituting the skin-color region extracted from time-sequential captured images, and generates a time series data of the representative value (here, an average value of respective pixels) of the pixel value as the pulse signal. In this case, it is possible to generate the time series data based on a pixel value of only a green component (G) that is particularly greatly changed due to a pulsation.

The generated time series data of the pixel value (average value) is accompanied by a minute fluctuation (for example, a fluctuation in pixel value being less than 1 gradation) according to a change of a concentration of hemoglobin in blood, for example, as illustrated in (A) of FIG. 3. Here, pulse calculator 23 executes a known filtering (for example, processing by a band pass filter in which a predetermined pass band is set) with respect to the time series data based on the pixel values. Accordingly, pulse calculator 23 can extract the pulse wave from which a noise component is removed as the pulse signal, as illustrated in (B) of FIG. 3. Further, pulse calculator 23 can calculate the pulse rate from the time between two or more peaks (or zero points) adjacent in the pulse wave.

As will be described below, pulse calculator 23 calculates the pulse of human H based on the skin-color region of captured image which is obtained by imaging with camera 2 after zoom commander 28 transmits the zoom command to camera 2 (that is, after the face region in the captured image is adjusted to have a suitable size). A method used by pulse calculator 23 is not limited to the method above described. Pulse calculator 23 may calculate (estimate) the pulse rate using other known methods. For example, it is possible to have a configuration in which the maximum value of spectrum acquired by frequency analysis (fast Fourier transform) of the time series data as illustrated in (A) of FIG. 3 is calculated as the pulse rate.

Region determiner 26 acquires the data of the number of pixels in the skin-color region from region extractor 22, and compares the data with a threshold value of the preset number of pixels. Here, two threshold values of the upper limit and the lower limit of the number of pixels (hereinafter, respectively referred to as the upper limit threshold value and lower limit threshold value) are set. Region determiner 26 compares the number of pixels of the skin-color region with upper limit threshold value and lower limit threshold value. Threshold value of the number of pixels in region determiner 26 is a value for determining the reference range of the number of pixels for acquiring the satisfactory pulse signal in pulse calculator 23.

That is, in a case where the number of pixels of the skin-color region is smaller than the lower limit threshold value, captured image suitable for extracting the pulse signal (refer to (A) and (B) of FIG. 3) in pulse calculator 23 cannot be acquired (that is, required number of pixels cannot be secured), and it becomes difficult to accurately estimate the pulse rate. On the other hand, in a case where the number of pixels of the skin-color region is greater than the upper limit threshold value, even if the required number of pixels can be secured, the pulse signal greatly fluctuates depending on the movement of human H, and it is difficult to accurately estimate the pulse rate in some cases. The determination result (that is, comparison result between the number of pixels of the skin-color region and threshold value) of region determiner 26 is transmitted to zoom commander 28. It is possible to determine the reference range of the number of pixels using only the lower limit threshold value without using the upper limit threshold value.

Data storage unit 27 stores the data of the upper limit threshold value and the lower limit threshold value described above. These upper limit threshold value and lower limit threshold value are stored as different values according to image sensor information on the performance and the like of the image sensor provided in camera 2, exposure information on an exposure condition and the like of camera 2 at the time of imaging, and signal processing information of camera 2. For example, an amount of saturation electrons, a dark current, and the like which affect noise can be used as the image sensor information of camera 2. Shutter speed, a diaphragm value, ISO sensitivity, and the like can be used as the exposure information. Each parameter and the like relating to the signal processing (correcting process) of image capturer 11 of camera 2 can be used as the signal processing information. Here, the upper limit threshold value and the lower limit threshold value are set based on the image sensor information, the exposure information, and the signal processing information; however, it is also possible to set the upper limit threshold value and the lower limit threshold value based on at least some of the information.

As the image sensor information of camera 2, information input by the user in advance can be used. Region determiner 26 can set the upper limit threshold value and the lower limit threshold value according to the information input by the user. In addition, regarding the exposure information and the signal processing information of camera 2, it is possible to use each information that is transmitted from camera 2 to pulse estimation device 3.

In a case where region determiner 26 determines that the number of pixels of the skin-color region is smaller than the lower limit threshold value, zoom commander 28 transmits a zoom-in command to zoom controller 12 of camera 2 as the zoom command so as to magnify the size (here, the number of pixels) of the skin-color region in the captured image to the appropriate size. Zoom controller 12 causes the lens driver in zoom lens mechanism 5 to execute the zoom-in operation based on the zoom-in command. For example, captured image P that is determined as the number of pixels of face region R being smaller than the lower limit threshold value by region determiner 26 as illustrated in FIG. 4A, is magnified to the size suitable for extracting the pulse signal by the zoom-in operation of camera 2 as illustrated in FIG. 4C.

On the other hand, in a case where region determiner 26 determines that the number of pixels of the skin-color region is greater than the upper limit threshold value, zoom commander 28 transmits a zoom-out command to zoom controller 12 of camera 2 as the zoom command so as to reduce the size of the skin-color region in the captured image to the appropriate size. Zoom controller 12 causes the lens driver in zoom lens mechanism 5 to execute the zoom-out operation based on the zoom-out command. For example, the captured image determined as the number of pixels of the skin-color region being greater than the upper limit threshold value by region determiner 26 as illustrated in FIG. 4B is reduced to the appropriate size for extracting the pulse signal as illustrated in FIG. 4C by the zoom-out operation of camera 2.

In addition, zoom commander 28 can cause information on a required amount (magnification ratio or reduction ratio of the skin-color region) for zoom-in or zoom out with respect to camera 2 to include to the zoom command based on the determination result of region determiner 26. It is also possible to adopt a configuration in which camera 2 (zoom controller 12) executes a zoom-in or zoom-out operation by a preset specific amount at the time of receiving one zoom command from the zoom commander 28, and zoom commander 28 repeats the transmission (that is, zoom-in or zoom-out operation as the specific amount) of the zoom command to camera 2 until the size of the skin-color region satisfies the preset reference range.

Face region R is illustrated by quadrangle in FIGS. 4A to 4C; however, the skin-color region extracted by region extractor 22 can be shown, for example, by setting an outline of the face excluding the head as an outer edge.

Pulse estimation device 3 as described above can be configured by an information processing device such as personal computer (PC). Although details are not illustrated, pulse estimation device 3 have a hardware configuration that includes a central processing unit (CPU) overall executing various information processing, controlling for peripherals, and the like according to a predetermined control program, a random access memory (RAM) functioning as a work area and the like of the CPU, a read only memory (ROM) storing a control program executed by the CPU or a data, a network interface executing a communicating process via a network, monitor (image output device), a speaker, an input device, a hard disk drive (HDD), and the like. At least some of functions of each portion of pulse estimation device 3 illustrated in FIG. 2 can be realized by executing a predetermined control program by the CPU. At least some of functions of pulse estimation device 3 may be substituted with a processing by other known hardware.

Figure 5:
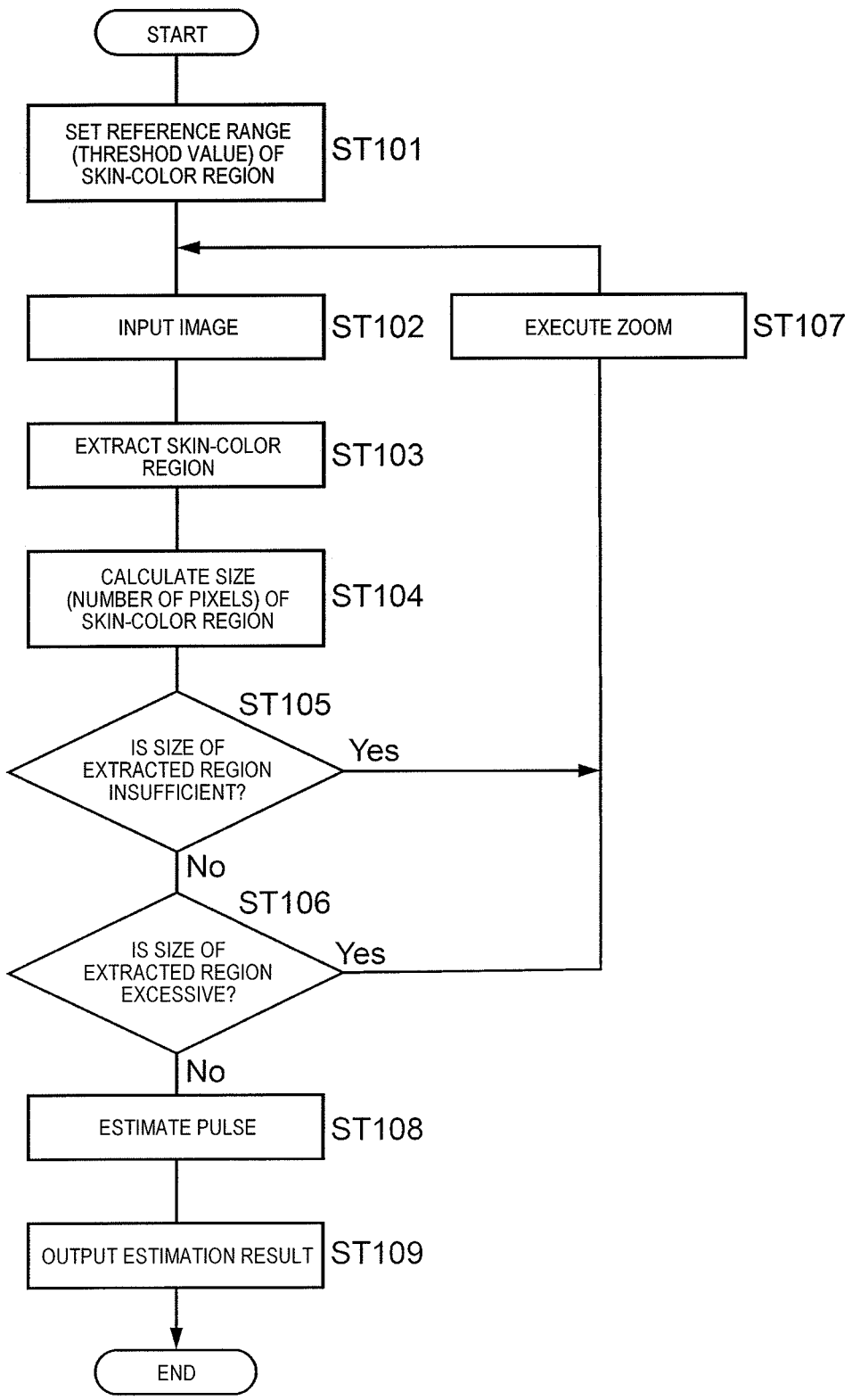
FIG. 5 is a flow chart illustrating a flow of process executed by the pulse estimation device of the first embodiment.

FIG. 5 is a flow chart illustrating a flow of a process executed by the pulse estimation device 3 of the first embodiment. First, region determiner 26 sets a threshold value (here, upper limit threshold value and lower limit threshold value), from the threshold data stored in data storage unit 27, for determining whether or not the size of the skin-color region extracted by region extractor 22 satisfies the preset reference range (ST101). Here, data storage unit 27 stores a threshold value table containing a plurality of threshold values which are set according to each data relating to various image sensor information, exposure information, and signal processing information. Region determiner 26 can select a corresponding threshold value from the threshold value table according to image sensor information, exposure information, and signal processing information of camera 2 used for imaging. Region determiner 26 may calculate a value of the threshold value from a predetermined calculating process using the image sensor information, the exposure information, and the signal processing information as a variable, instead of using the threshold value table.

Next, in a case where the captured image (frame image) is input to image input portion 21 from camera 2 (ST102), region extractor 22 extracts the skin-color region in the captured image (ST103) and calculates the size (here, number of pixels) of the skin-color region (ST104). Region determiner 26 compares the number of pixels of the skin-color region, calculated by region extractor 22 with the lower limit threshold value set in step ST101 (ST105). In a case where the number of pixels of the skin-color region is smaller than the lower limit threshold value (ST105: Yes), zoom commander 28 transmits the zoom-in command to zoom controller 12 of camera 2. Accordingly the zoom-in operation by a predetermined amount is executed in camera 2 (ST107).

On the other hand, in a case where it is determined that the number of pixels of the skin-color region is equal to or greater than the lower limit threshold value in step ST105 (No), region determiner 26 further compares the number of pixels of the skin-color region with the upper limit threshold value set in step ST101 (ST106). In a case where the number of pixels of the skin-color region is greater than the upper limit threshold value (ST106: YES), zoom commander 28 transmits the zoom-out command to zoom controller 12 of camera 2. Accordingly, the zoom-out operation by a predetermined amount is executed in camera 2 (ST107).

Next, pulse calculator 23 calculates the pulse of human H based on the skin-color region of the captured image which is imaged by camera 2 after zoom commander 28 transmits the zoom command to camera 2 (that is, after the size of the skin-color region is appropriately adjusted) (ST108). In a case where it is not necessary that the zoom operation is executed in step ST107 (that is, in a case where the size of the skin-color region satisfies the reference range between the lower limit threshold value and the upper limit threshold value without requiring execution of the zoom operation), pulse calculator 23 calculates the pulse without changing the size of the skin-color region of the captured image.

Then, pulse calculator 23 outputs the pulse calculation result to display 24. Accordingly, the estimated pulse rate and the wave form of the pulse wave (refer to (B) of FIG. 3) are displayed with respect to the user (ST109).

In pulse estimation device 3, above-described steps ST102 to ST109 are executed repeatedly with respect to the captured images sequentially input from camera 2.

Second Embodiment

Figure 6:
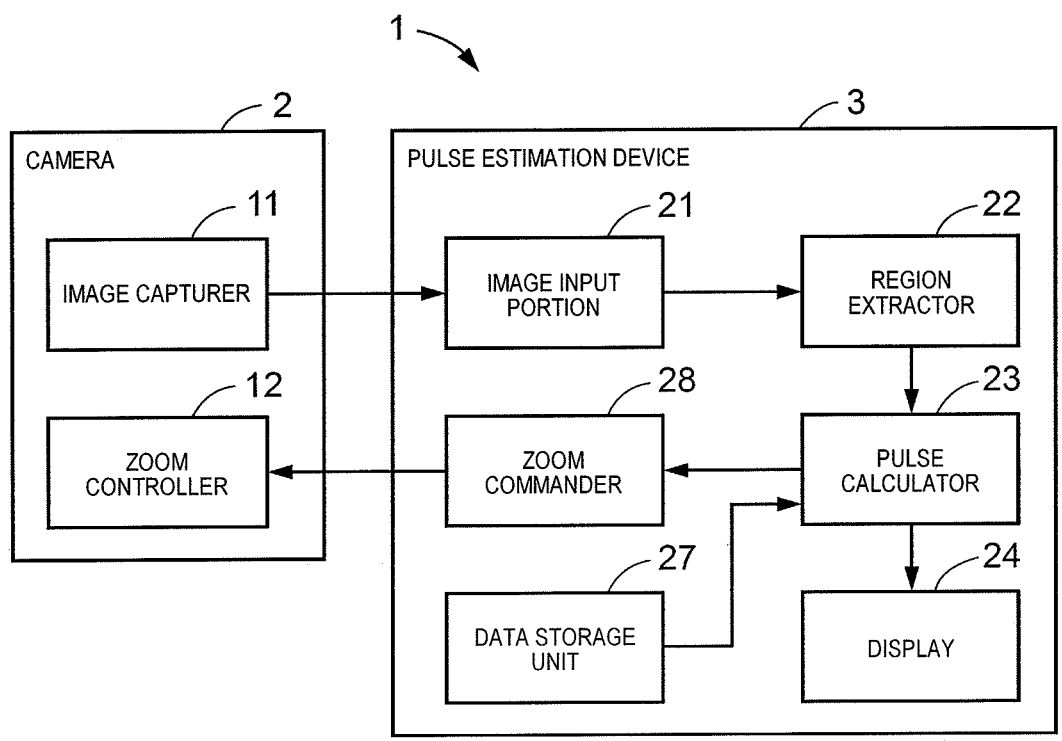
FIG. 6 is a functional block diagram of a pulse estimation system of a second embodiment.

FIG. 6 is a functional block diagram of pulse estimation system 1 of the second embodiment of the present disclosure. FIGS. 7A and 7B are explanatory diagrams of the pulse extracting process executed by a pulse calculator 23 of pulse estimation device 3. FIGS. 8A and 8B are explanatory diagrams illustrating a modification example of the pulse determining process shown in FIGS. 7A and 7B. In FIG. 6 to FIG. 8B, the same configuration elements as those of the above described first embodiment are denoted by the same reference marks. In addition, in the second embodiment, the matters especially not stated in the following are the same as the case of the above described first embodiment.

Since pulse estimation system 1 of the second embodiment determines whether or not adjustment of the size of the skin-color region extracted by region extractor 22 is necessary, pulse estimation system 1 is different from the case of the first embodiment, in view of performing the determination in pulse calculator 23 instead of determination by region determiner 26 of the above described first embodiment.

Pulse calculator 23 extracts the pulse wave in the same manner as in the case of the above described first embodiment. Further, pulse calculator 23 determines whether or not the extracted pulse wave is stable. For example, in a case where the stable pulse wave is extracted in pulse calculator 23 as shown in FIG. 7A, zoom commander 28 determines that the adjustment of the size of the skin-color region extracted by region extractor 22 is not necessary, and thus does not transmit the zoom command to camera 2.

On the other hand, for example, in a case where an unstable pulse wave is extracted in pulse calculator 23 as shown in FIG. 7B, zoom commander 28 transmits the zoom command to camera 2. In this case, zoom commander 28 transmits the zoom-in command as the zoom command. In a case where the stable pulse wave is not extracted in pulse calculator 23 even after the zoom-in command is transmitted, zoom commander 28 can switch the zoom command to the zoom-out command.

Data storage unit 27 stores the data of a reference wave form relating to the stable pulse wave prepared in advance. Pulse calculator 23 can determine whether or not the pulse wave is stable by executing a matching process between the reference wave form and the extracted pulse wave. Pulse calculator 23 may extract a peak value of the extracted pulse wave, and determine stability of pulse wave based on the magnitude (fluctuation amount) of the peak values during a certain period of time.

In addition, the pulse determining process executed by pulse calculator 23 is not limited to a process based on the wave form of the pulse wave as described above. The pulse determining process may be a process based on a temporal change of the pulse wave calculated from the pulse wave. For example, in a case where the pulse rate calculated in pulse calculator 23 is stable (where a fluctuation amount of the pulse rate continuous during the certain period time does not exceed a preset threshold value) as shown in FIG. 8A, zoom commander 28 determines that the adjustment of the size of the skin-color region extracted by region extractor 22 is not necessary, and thus does not transmit the zoom command to camera 2. On the other hand, in a case where the pulse rate is unstable (where the fluctuation amount of the pulse rate continuous during the certain period of time exceeds the preset threshold value) as shown in FIG. 8B, zoom commander 28 transmits the zoom command to camera 2.

Figure 9:
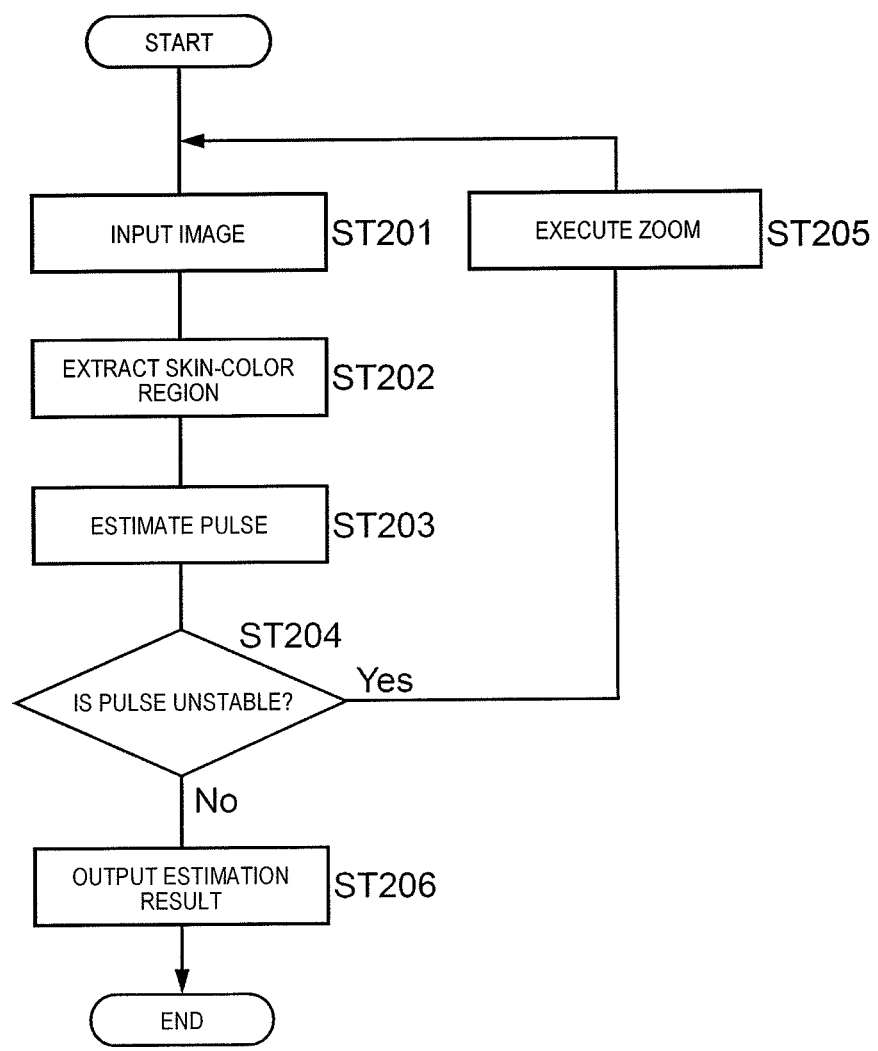
FIG. 9 is a flow chart illustrating a flow of process executed by the pulse estimation device of the second embodiment.

FIG. 9 is a flow chart illustrating a flow of process executed by pulse estimation device 3 of the second embodiment. In pulse estimation device 3, steps ST201 and ST202 respectively similar to steps ST102 and ST103 shown in above described FIG. 5 are firstly executed.

Next, pulse calculator 23 calculates (estimates) the pulse wave of human H based on the captured image before the zoom command is transmitted (ST203). Pulse calculator 23 determines whether or not the pulse wave extracted in step ST203 is unstable (ST204). In a case where the pulse wave is determined as unstable (ST204: Yes), zoom commander 28 transmits the zoom command to camera 2. Accordingly, the zoom-in operation by the predetermined amount is executed in camera 2 (ST205).

Finally, in a case where the pulse wave is determined as stable in step ST204, the estimated pulse rate and the wave form of the pulse wave is displayed with respect to the user (ST206).

Third Embodiment

Figure 10:
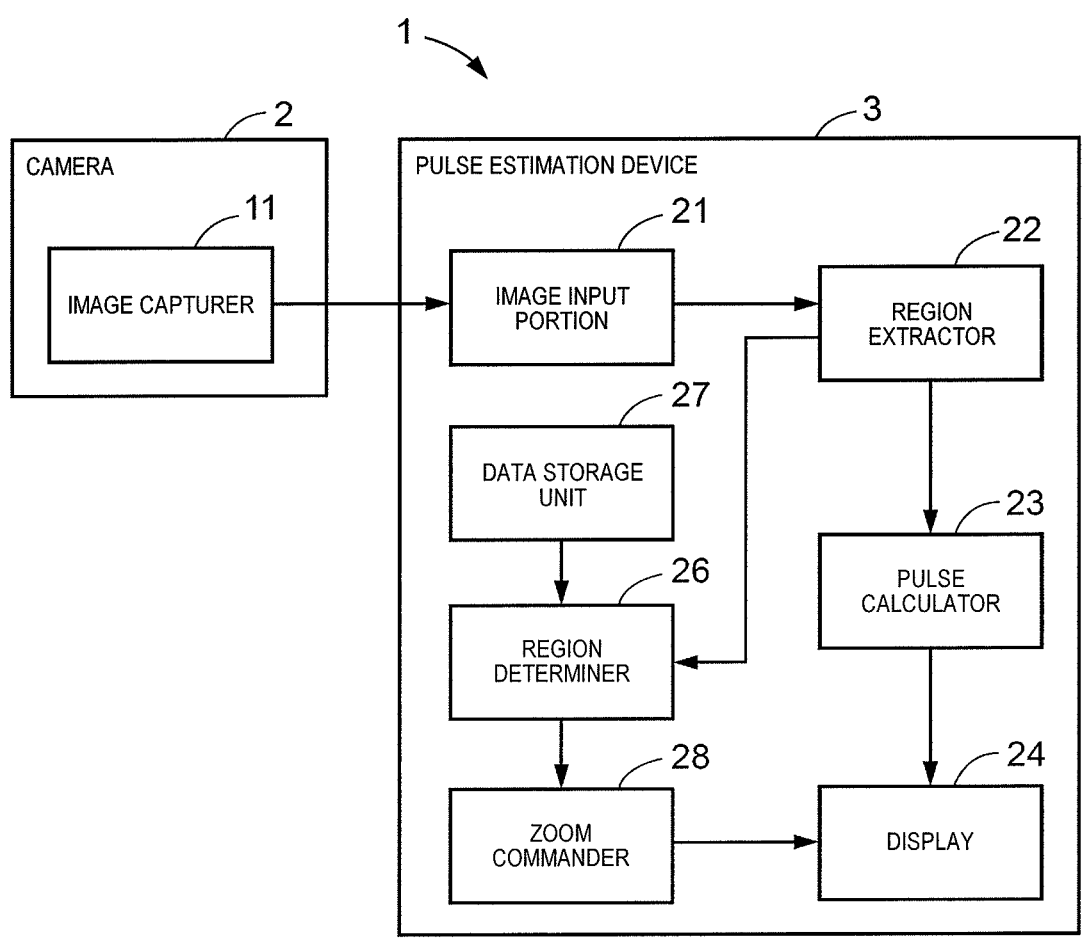
FIG. 10 is a functional block diagram of a pulse estimation system of a third embodiment.

FIG. 10 is a functional block diagram of pulse estimation system 1 of the third embodiment of the present disclosure.

Figure 11A:
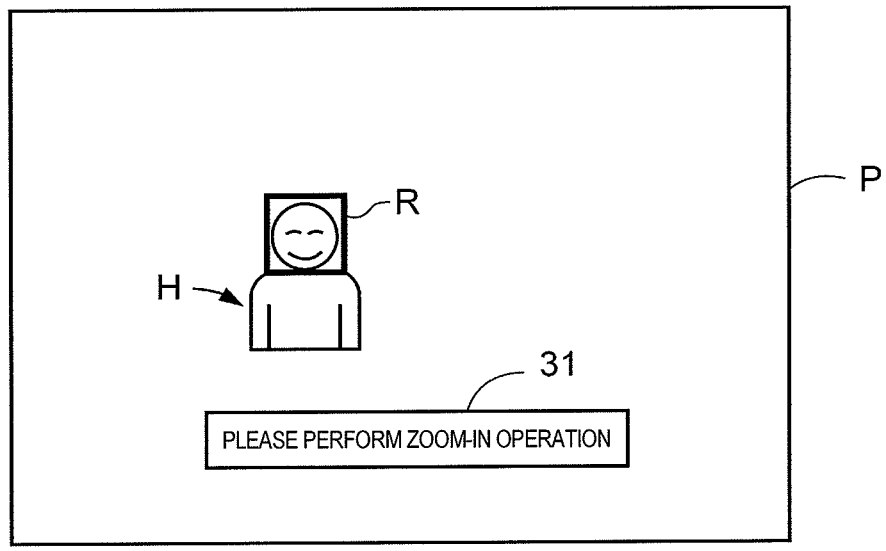
FIG. 11A is an explanatory diagram illustrating an example of an operation instruction of a zoom commander of a pulse estimation device shown in FIG. 10.
Figure 11B:
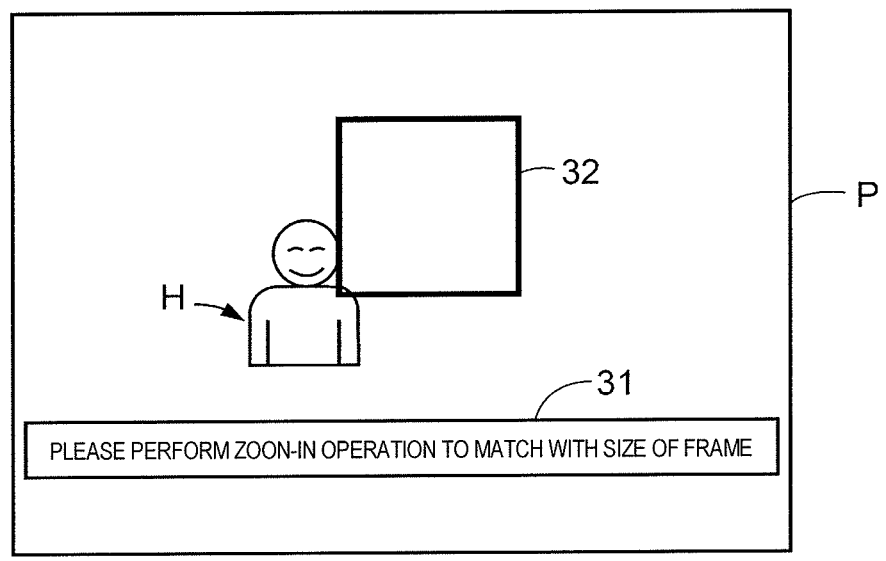
FIG. 11B is an explanatory diagram illustrating an example of an operation instruction of the zoom commander of the pulse estimation device shown in FIG. 10.

FIGS. 11A and 11B are explanatory diagrams illustrating examples of an operation instruction of zoom commander 28 of pulse estimation device 3 shown in FIG. 10. In FIG. 10 and FIGS. 11A and 11B, the same configuration elements as those of the above described first or second embodiment are denoted by the same reference marks. In addition, in the third embodiment, the matters especially not stated in the following are the same as the case of the above described first or second embodiment.

Pulse estimation system 1 of the third embodiment is different from the case of the first embodiment, in view of transmitting the zoom command to a user of pulse estimation device 3 by zoom commander 28 instead of transmitting the zoom command to camera 2.

For example, in a case where region determiner 26 determines that the number of pixels of the skin-color region is smaller than the lower-limit threshold value, zoom commander 28 transmits the zoom-in command to the user as the zoom command so as to magnify the size of the skin-color region in the captured image to the appropriate size. Display 24 outputs the operation instruction urging the user to perform the predetermined zoom operation based on the zoom-in command from zoom commander 28. For example, in captured image P that is determined as the number of pixels of face region R being smaller than the lower limit threshold value by region determiner 26 as illustrated in FIG. 11A, zoom operation instruction 31 is displayed so as to urge the user to perform the zoom operation (here, zoom-in operation). Accordingly, the zoom-in operation of camera 2 is executed by the user.

As another method, for example, as shown in FIG. 11B, a method may be configured such that display frame 32 showing a reference of an operation amount of the zoom operation to be performed by the user is displayed, and zoom operation instruction 31 is displayed so as to urge the user to match the size of the face of human H with the display frame 32.

Fourth Embodiment

Figure 12:
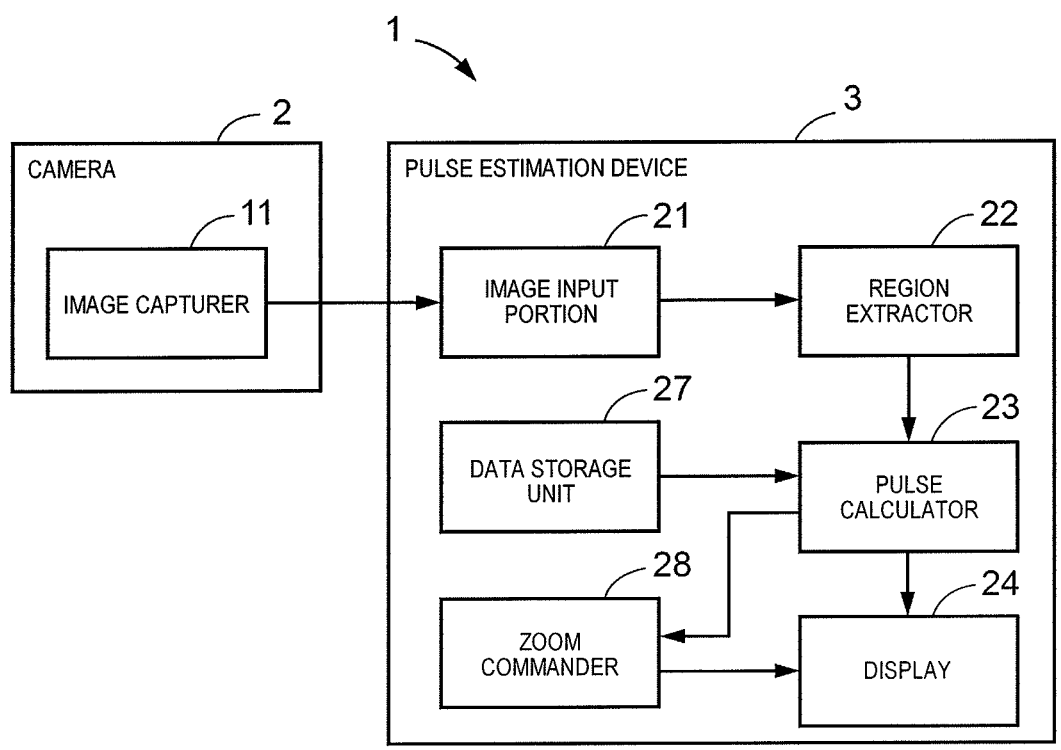
FIG. 12 is a functional block diagram of a pulse estimation system of a fourth embodiment.

FIG. 12 is a functional block diagram of a pulse estimation system 1 of a fourth embodiment of the disclosure. In FIG. 12, the same configuration elements as those of any of the above described first to third embodiments are denoted by the same reference marks. In addition, in the fourth embodiment, the matters especially not stated in the following are the same as the case of any of the above described first to third embodiments.

Pulse estimation system 1 of the fourth embodiment is different from the case of the second embodiment, in view of transmitting the zoom command to a user of pulse estimation device 3 by zoom commander 28 instead of transmitting the zoom command to camera 2.

For example, in a case where pulse calculator 23 extracts the unstable pulse, zoom commander 28 transmits the zoom-in command to the user as the zoom command so as to magnify the size of the skin-color region in the captured image to the appropriate size. The operation instruction urging the user to perform the predetermined zoom operation to similar to the case of the third embodiment is output on display 24.

Hereinabove, the present disclosure is described based on specific embodiments; however, these embodiments are merely examples. The present disclosure is not limited to these embodiments. For example, the pulse estimation device, the pulse estimation system, and the pulse estimation method of the present disclosure are not limited to a medical use. It is possible to apply to various use of monitoring (quarantine at an airport and the like), physical condition management of athletes, and the like. In addition, a configuration in which the camera and the pulse estimation device are provided is exemplified in the embodiments; however, it is possible to adopt a configuration in which either the camera or pulse estimation device has at least some of functions of the other. Every component of the pulse estimation device, the pulse estimation system, and the pulse estimation method is not necessarily essential, it is possible to appropriately select the component as long as at least it does not depart from the scope of the present disclosure.

INDUSTRIAL APPLICABILITY

The pulse estimation device, the pulse estimation system, and the pulse estimation method of the present disclosure are useful as a pulse estimation device, a pulse estimation system, and a pulse estimation method that can stably estimate a pulse based on the image data suitable for extracting a pulse signal and estimate the pulse of a human body from information obtained without contact with the human body.

REFERENCE MARKS IN THE DRAWINGS

1 Pulse Estimation System
2 Camera
3 Pulse Estimation Device
5 Zoom Lens Mechanism
11 Image Capturer
12 Zoom Controller
21 Image Input Portion
22 Region Extractor
23 Pulse Calculator (Pulse Estimator)
24 Display
26 Region Determiner
27 Data Storage Unit
28 Zoom Commander
H Human (Object)
P Captured Image
R Face Region

The invention claimed is:

1. A pulse estimation device that estimates a pulse of a subject from information obtained without contact with the subject, the pulse estimation device comprising:
a processor;
a memory including instructions that, when executed by the processor, cause the processor to perform operations including:
inputting time-sequential captured images including at least a portion of the subject as an object from a camera;
extracting a skin-color region from each of the captured images;
transmitting a zoom command to the camera that has imaged the captured images or a user of the camera in order to adjust a size of the skin-color region; and
estimating the pulse of the subject based on the skin-color region of the captured images obtained by imaging with the camera, after the zoom command is transmitted,
wherein the operations further include estimating the pulse of the subject based on the captured images before the zoom command is transmitted, and determining whether or not the estimated pulse is stable, and in a case where the estimated pulse is not stable, transmitting the zoom command.

2. The pulse estimation device of claim 1, wherein the operations further include:
   determining whether or not the size of the skin-color region satisfies a preset reference range, and
   in a case that the size of the skin-color region does not satisfy the preset reference range, transmitting the zoom command to the camera or the user of the camera.

3. The pulse estimation device of claim 2, wherein the operations further include:
   determining the size of the skin-color region based on a number of pixels constituting the skin-color region of the captured image; and
   determining whether or not the size of the skin-color region satisfies the preset reference range based on the number of pixels.

4. The pulse estimation device of claim 2, wherein the operations further include:
   changing the preset reference range according to a performance of an image sensor of the camera.

5. The pulse estimation device of claim 2, wherein the operations further include:
   changing the preset reference range according to an exposure condition of the camera.

6. The pulse estimation device of claim 1, wherein the operations further include:
   extracting a face region of the subject from each of the captured images as the skin-color region.

7. The pulse estimation device of claim 1, further comprising:
   a display that displays a command for adjusting the size of the skin-color region to the user based on the zoom command to the user.

8. A pulse estimation system comprising:
   the pulse estimation device of claim 1; and
   the camera that performs a predetermined zoom operation based on the zoom command.

9. A pulse estimation method of estimating a pulse of a subject from information obtained without contact with the subject, the pulse estimation method comprising:
   inputting time-sequential captured images including at least a portion of the subject as an object from a camera;
   extracting a skin-color region from each of the captured images;
   transmitting a zoom command to the camera that has imaged the captured images or a user of the camera in order to change a size of the skin-color region such that the size of the skin-color region satisfies a preset reference range; and
   estimating the pulse of the subject based on the skin-color region of the captured images obtained by imaging with the camera, after the zoom command is transmitted,
   wherein the pulse estimation method further comprises:
      estimating the pulse of the subject based on the captured images before the zoom command is transmitted, and determining whether or not the estimated pulse is stable, and
      in a case where the estimated pulse is not stable, transmitting the zoom command.

10. A pulse estimation device that estimates a pulse of a subject from information obtained without contact with the subject, the pulse estimation device comprising:
   a processor;
   a memory including instructions that, when executed by the processor, cause the processor to perform operations including:
      inputting time-sequential captured images including at least a portion of the subject as an object from a camera;
      extracting a skin-color region from each of the captured images;
      transmitting a zoom command to the camera that has imaged the captured images or a user of the camera in order to adjust a size of the skin-color region; and
      estimating the pulse of the subject based on the skin-color region of the captured images obtained by imaging with the camera, after the zoom command is transmitted,
   wherein the operations further include determining whether or not the size of the skin-color region satisfies a preset reference range,
   in a case that the size of the skin-color region does not satisfy the preset reference range, transmitting the zoom command to the camera or the user of the camera, and
   the operations even further include:
      determining the size of the skin-color region based on a number of pixels constituting the skin-color region of the captured image; and
      determining whether or not the size of the skin-color region satisfies the preset reference range based on the number of pixels.

11. A pulse estimation method of estimating a pulse of a subject from information obtained without contact with the subject, the pulse estimation method comprising:
   inputting time-sequential captured images including at least a portion of the subject as an object from a camera;
   extracting a skin-color region from each of the captured images;
   transmitting a zoom command to the camera that has imaged the captured images or a user of the camera in order to change a size of the skin-color region such that the size of the skin-color region satisfies a preset reference range; and
   estimating the pulse of the subject based on the skin-color region of the captured images obtained by imaging with the camera, after the zoom command is transmitted,
   wherein the pulse estimation method further comprises determining whether or not the size of the skin-color region satisfies a preset reference range,
   in a case that the size of the skin-color region does not satisfy the preset reference range, transmitting the zoom command to the camera or the user of the camera, and
   the pulse estimation method even further comprises:
      determining the size of the skin-color region based on a number of pixels constituting the skin-color region of the captured image; and
      determining whether or not the size of the skin-color region satisfies the preset reference range based on the number of pixels.

12. A pulse estimation device that estimates a pulse of a subject from information obtained without contact with the subject, the pulse estimation device comprising:
   a processor;
   a memory including instructions that, when executed by the processor, cause the processor to perform operations including:

inputting time-sequential captured images including at least a portion of the subject as an object from a camera;

extracting a skin-color region from each of the captured images;

transmitting a zoom command to the camera that has imaged the captured images or a user of the camera in order to adjust a size of the skin-color region; and estimating the pulse of the subject based on the skin-color region of the captured images obtained by imaging with the camera, after the zoom command is transmitted, wherein the operations further include determining whether or not the size of the skin-color region satisfies a preset reference range, in a case that the size of the skin-color region does not satisfy the preset reference range, transmitting the zoom command to the camera or the user of the camera, and the operations even further include changing the preset reference range according to a performance of an image sensor of the camera.

13. A pulse estimation method of estimating a pulse of a subject from information obtained without contact with the subject, the pulse estimation method comprising:

inputting time-sequential captured images including at least a portion of the subject as an object from a camera;

extracting a skin-color region from each of the captured images;

transmitting a zoom command to the camera that has imaged the captured images or a user of the camera in order to change a size of the skin-color region such that the size of the skin-color region satisfies a preset reference range; and estimating a pulse of the subject based on the skin-color region of the captured images obtained by imaging with the camera, after the zoom command is transmitted, wherein the pulse estimation method further comprises determining whether or not the size of the skin-color region satisfies a preset reference range, in a case that the size of the skin-color region does not satisfy the preset reference range, transmitting the zoom command to the camera or the user of the camera, and the pulse estimation method even further comprises changing the preset reference range according to a performance of an image sensor of the camera.

* * * * *